US006965708B2

(12) United States Patent
Luo et al.

(10) Patent No.: US 6,965,708 B2
(45) Date of Patent: Nov. 15, 2005

(54) DEVICES, SYSTEMS, AND METHODS FOR SENSING MOISTURE

(75) Inventors: Shufang Luo, Blacksburg, VA (US); Jennifer L. Elster, Blacksburg, VA (US); Yongcheng Liu, Blacksburg, VA (US); Artur Sucheta, Lebanon, NH (US)

(73) Assignee: Luna Innovations, Inc., Blacksburg, VA (US)

( * ) Notice: Subject to any disclaimer, the term of this patent is extended or adjusted under 35 U.S.C. 154(b) by 317 days.

(21) Appl. No.: 10/264,507

(22) Filed: Oct. 4, 2002

(65) Prior Publication Data

US 2005/0105841 A1 May 19, 2005

(51) Int. Cl.⁷ .................................................. G02B 6/00
(52) U.S. Cl. ............................. 385/12; 385/13; 385/37; 385/123; 385/128
(58) Field of Search ............................ 385/12, 13, 37, 385/147, 123–128; 250/227.14, 227.17, 227.18; 340/555–557; 73/73–77

(56) References Cited

U.S. PATENT DOCUMENTS

| | | |
|---|---|---|
| 4,221,962 A | 9/1980 | Black |
| 4,634,856 A | 1/1987 | Kirkham |
| 4,749,856 A | 6/1988 | Walker |
| 4,812,014 A | 3/1989 | Sawano |
| 4,834,497 A | 5/1989 | Angel |
| 4,894,532 A | 1/1990 | Peterson |
| 5,138,153 A | 8/1992 | Gergely |
| 5,243,670 A | 9/1993 | Bonicel |
| 5,315,673 A | 5/1994 | Stetter |
| 5,319,975 A | 6/1994 | Pederson |
| 5,440,927 A | 8/1995 | Chu |
| 5,641,956 A | 6/1997 | Vengsarkar |
| 5,864,641 A | 1/1999 | Murphy |
| 6,021,240 A | 2/2000 | Murphy |
| 6,035,082 A | 3/2000 | Murphy |
| 6,205,263 B1 | 3/2001 | Lieberman |
| 6,275,628 B1 | 8/2001 | Jones |
| 6,343,168 B1 | 1/2002 | Murphy |
| 6,691,007 B2 * | 2/2004 | Haugse et al. ................ 701/29 |
| 2002/0018629 A1 | 2/2002 | Lieberman |

FOREIGN PATENT DOCUMENTS

| | | |
|---|---|---|
| EP | 0 335 128 A3 | 10/1989 |
| JP | 61217744 A | 9/1986 |
| JP | 01292237 A | 11/1989 |

OTHER PUBLICATIONS

Jennifer Elster et al., "Optical Fiber–Based Chemical Sensors for Detection of Corrosion Precursors and By–Products", SPIE, Nov. 1, 1998, 7 pages, Boston, MA.
Jennifer L. Elster et al., "Corrosion Monitoring in Aging Aircraft Using Optical Fiber–Based Chemical Sensors", Fourth Joint DoD/FAA/NASA Conference on Aging Aircraft, May 1, 2000, pp. 1–8, St. Louis, MO.
Jennifer L. Elster, "Long Period Grating–Based PH Sensors for Corrosion Monitoring", Thesis submitted to the Faculty of the Virginia Polytechnic Institute and State University, May 19, 1999, pp. i–v and 1–47, Blacksburg, Virginia.

* cited by examiner

*Primary Examiner*—Akm Enayet Ullah
*Assistant Examiner*—Kevin S. Wood
(74) *Attorney, Agent, or Firm*—Michael Haynes PLC

(57) ABSTRACT

Various exemplary embodiments, devices, systems, and methods for sensing moisture are disclosed, including at least one moisture sensor that comprises an optical fiber, a long period grating formed in at least a portion of the optical fiber, and a layer of PEI bonded to the long period grating. One exemplary embodiment comprises a system for measuring humidity, the system comprising an optical fiber moisture sensor having a mono-layer of PEI covalently-bonded to an outer surface of said optical fiber, a processor coupled to said optical fiber moisture sensor, and a moisture indicator coupled to said processor.

40 Claims, 13 Drawing Sheets

DEVICES, SYSTEMS, AND METHODS FOR SENSING MOISTURE

BRIEF DESCRIPTION OF THE DRAWINGS

Certain embodiments of the invention will be more readily understood through the following detailed description, with reference to the accompanying drawings, in which.

DETAILED DESCRIPTION

Figure 1:
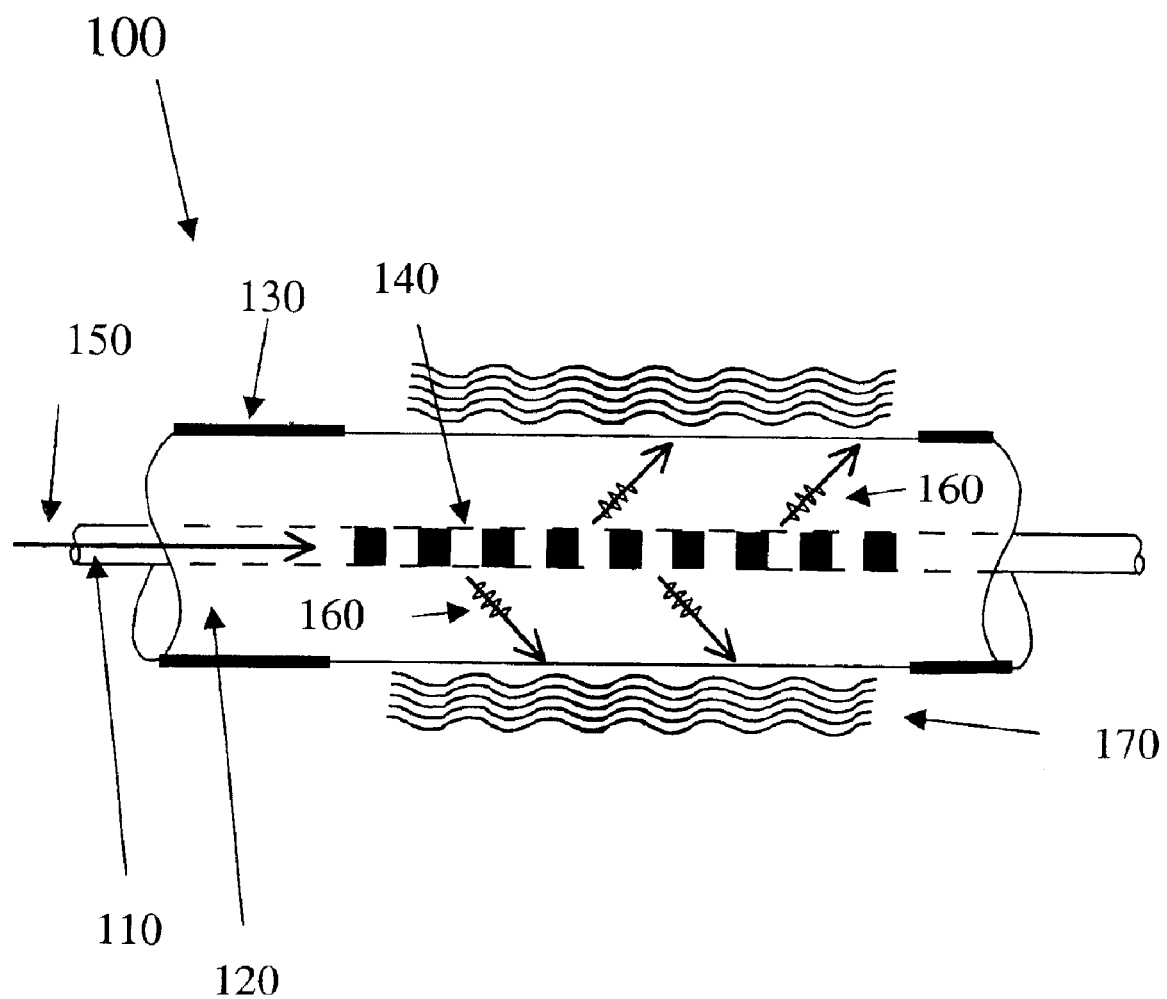
FIG. 1 is a schematic diagram of an embodiment of an exemplary fiber optic sensor of the present invention.

Certain exemplary embodiments of the present invention comprise a device, system, and/or method that can sense moisture.

Certain exemplary embodiments comprises a system for measuring humidity, the system comprising an optical fiber moisture sensor having a mono-layer of PEI covalently-bonded to an outer surface of said optical fiber, a processor coupled to said optical fiber moisture sensor, and a moisture indicator coupled to said processor.

Certain exemplary embodiments of the present invention comprise a moisture sensor that comprises an optical fiber, a long period grating formed in at least a portion of the optical fiber, and a layer of PEI bonded to the long period grating.

A layer of a polymer, such as polyethylenimine ("PEI"), can absorb moisture in an environment by forming hydrogen bonds, which can cause the polymer layer to swell, resulting in a change of the polymer layer's density, thickness, and index of refraction. Thus, a layer of PEI polymer can be sensitive to moisture, which can include water vapor and/or liquid, such as humidity, condensation, and/or an aqueous puddle.

The PEI polymer can be attached covalently to the outer surface of a cladding surrounding a long-period grating ("LPG") on an optical fiber. Due to the PEI coating, the light transmission, propagation, scattering, and/or refraction characteristics of the optical fiber can change as a function of moisture conditions in an environment to which the coating is exposed. By sensing the moisture changes in the environment, the coated optical fiber can serve as a sensor that can measure moisture reversibly and repeatably for long-term use.

The moisture sensor can include an optical waveguide or fiber that, in some embodiments, can be fabricated from photosensitive germania-doped fused-silica glass. The moisture sensor can also include an LPG, which is a spectral loss element that can scatter light out of the core of the optical fiber, and into the cladding, coating, and/or environment. The wavelength of the scattered light can be determined by the grating period, the refractive index of the core, the refractive index of the cladding, the refractive index of the coating, and/or the refractive index of the environment surrounding the optical fiber.

The LPG, whose period L can be chosen to match the difference in effective refractive indices of the core and a propagating cladding mode, can allow coupling of light from a guided mode into forward propagating cladding modes where it can be lost due to absorption and scattering. Thus, light transmitted into the core of the optical fiber and through the LPG can be characterized by its loss band, that is, the frequencies of light that are missing due to scattering by the LPG.

A common way of imprinting an LPG onto the core of a fiber is to expose the fiber core to ultraviolet (UV) rays through a binary amplitude mask of spatial period L. An alternate method is to imprint the desired period L, point by point by translating the fiber relative to a focused UV light beam. In still another method of imprinting an LPG, 248 nm radiation from a KrF laser can be applied to the fiber through a slit or a mask rather than an amplitude mask. If a slit is used, the fiber can be moved to successive exposure sites.

The photosensitivity of a commercially available fiber can be enhanced by placing the fiber in a chamber filled with high-pressure hydrogen and thus hydrogen loading the fiber. Once the fiber is saturated, it can be stored at −80 degrees Celsius to prevent the hydrogen from leaking out. The fiber is then placed behind an amplitude mask containing a pattern with the desired period and a high-power 244 nm ultraviolet laser beam can be scanned across the mask striking the fiber at the spacing designated by the amplitude mask, thus raising the index of refraction at the locations "illuminated" by the laser. The resulting LPG can be monitored during is this process using a Laser Diode source and an Optical Spectrum Analyzer (available from Ando Electric CO. LTD., Japan) to ensure that the desired wavelength range is attenuated. In this manner, the attenuated wavelengths (i.e., loss bands) can be tailored by adjusting the periodic spacing of the amplitude mask. To ensure the stability of the LPG, the fiber can be annealed in a high-temperature oven to remove the remaining hydrogen from the fiber.

The resulting effect of this process is a periodically-spaced modulation of the refractive index of the fiber core that will couple optical wavelengths traveling through the core into cladding modes, causing a spectral loss at a certain wavelength ranges. Thus, the LPG can filter at several different optical wavelengths that light that is transmitted into the core of the fiber, thus creating a loss bands observable in an output spectrum of the fiber's core.

Over the completed LPG imprinted fiber, a monomolecular ("mono-layer") layer of polymer can be covalently bonded. The refractive index of the mono-layer can be sensitive to moisture.

The index of refraction of the moisture-absorbing polymer layer can impact the frequency ranges of the loss bands caused by the LPG. Consequently, the light output characteristics of such a coated optical fiber can reversibly change as a function of moisture conditions in an environment to which the coating is exposed. Thus, changes in moisture conditions can be sensed, detected, monitored, and/or measured by detecting, monitoring, and/or measuring the spectral shift in the wavelength and/or frequency of the loss band of the spectral output of the fiber's core.

FIG. 1 is a schematic diagram of an embodiment of an exemplary fiber optic is sensor 100 of the present invention. Sensor 100 can be used as a moisture sensor. Fiber core 110 is surrounded by cladding 120, which in turn is surrounded over at least a portion of the length of the fiber by a coating 130. A grating 140, such as a long period grating, is provided along at least a portion of the length of fiber core 110. A stream of photons 150 can enter one end of fiber core 110, and be guided and/or propagate through core 110. Upon striking grating 140, at least a portion of photons 150 can be coupled into cladding 120 and/or diverted as a plurality of photons 160 into cladding 120 and can possibly be emitted as photons 170 beyond moisture sensor 100. Another portion of photons 150 that strikes grating 140 can continue down fiber core 110.

Generally speaking, depending on the periodicity of the grating, a phase matching condition can be satisfied such that the forward propagating findamental mode can be coupled into propagating cladding modes and the evanescent field can extend out of the optical fiber. As with fiber Bragg gratings, the wavelengths affected can be limited. If the cladding is surrounded by air, then these cladding modes can be guided by the cladding-air interface, and they can propagate with little attenuation. If, however, the cladding is surrounded by a glossy polymer jacket, such as those used on normal telecommunications fibers, then the cladding modes can quickly attenuate and can be extinguished by the interaction of the light in the cladding mode with the glossy jacket.

The spectral location of a loss band can be a function of the difference in the effective indices of the guided mode and the corresponding cladding mode. The coupling wavelength $\lambda$ for a particular resonance band can be described by the following expression, $$\lambda = (n_g - n_{cl})\Lambda, \text{ Equation 1:}$$

where, $\Lambda$ is the grating period and $n_g$ and $n_{cl}$ are the effective refractive indices of the guided and cladding modes, respectively, that depend on the fiber parameters. Thus any variations in the values of $\Lambda$, $n_g$, or $n_{cl}$ can shift the position of the resonance band. By allowing only $n_{cl}$ to change with refractive index changes, real-time refractive index measurements can be correlated to measured target concentration.

Figure 2:
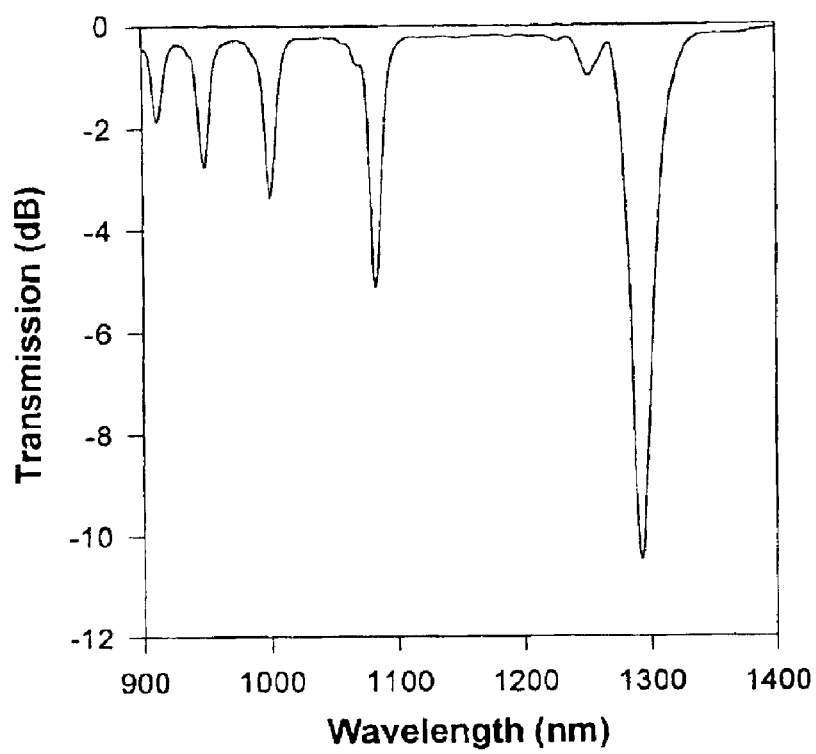
FIG. 2 is a transmission spectrum of an exemplary long period grating of the present invention.

FIG. 2 is a transmission spectrum of an exemplary long period grating of the present invention. This optical spectrum was measured by the Optical Spectrum Analyzer (available from Ando Electric CO. LTD., Japan), and was acquired by injecting broadband light into an optical fiber. The location of the spectral loss dip can be dependent on the grating period, the refractive index of the optical fiber's core, the refractive index of the cladding, and/or the surrounding refractive index. Tracking of local refractive index changes can be accomplished by tracking the location of the spectral loss dip.

Figure 3:
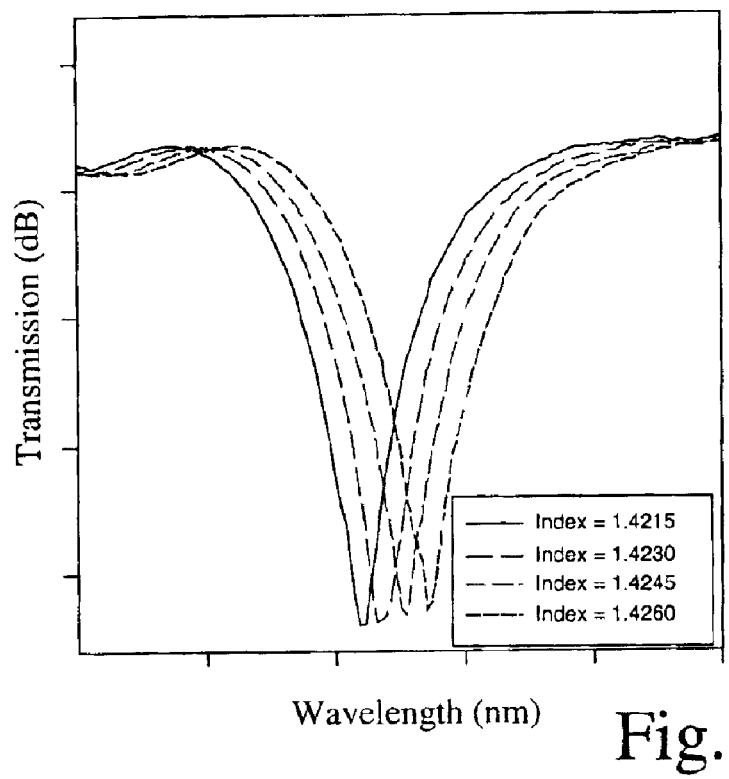
FIG. 3 is a transmission spectrum of an exemplary long period grating of the present invention.

FIG. 3 is a transmission spectrum of an exemplary long period grating of the present invention. FIG. 3 shows a representative spectral shift with refractive index change. The magnitude of the spectral shift can be tailored by adjusting the LPG fabrication parameters. By tracking this spectral shift, refractive index measurements on the order of $1 \times 10^{-6}$ can be achieved. This measurement can then be correlated to the concentration of environmental target such as moisture content or relative humidity.

Sensing and/or detecting changes in the concentration of one or more target materials, including one or more target substances, chemicals, mixtures, compounds, molecules, elements, atoms, biologicals, fungi, bacteria, viruses, and/or proteins can be accomplished by coating the LPG with a layer(s) that experiences a measurable change in refractive index in the presence of, and/or from a change in the concentration of, the target material(s). As the coating absorbs changing concentrations of the target material, the refractive index can change, causing a shift in the wavelength of the scattered light. For each LPG sensor, a coating can be applied to the surface of an LPG that is responsive to changes in concentration of at least the desired target, and can be optimized for specificity, sensitivity, and/or reliability.

PEI polymer coating has been found to be sensitive to moisture or relative humidity. The PEI polymer can be attached covalently to the surface of long-period grating (LPG) on an optical fiber and used to measure moisture or relative humidity reversibly and repeatably. Such LPG sensors have been tested for temperature range and effect for use with applications where temperature varies as humidity increases or decreases.

Testing of such sensors was performed in an effort to determine the effect of temperature on humidity readings, and the accuracy of such measurements in the air. The apparatus used was a Thunder Scientific Humidity Generator (available from Thunder Scientific Corp., Albuquerque, N. Mex.) that provides accurate controls of temperature and humidity levels. The sensors were tested in a chamber under several conditions such as: (i) keeping relative humidity constant while increasing or decreasing the temperature levels stepwise; or (ii) keeping temperature constant while increasing or decreasing relative humidity levels stepwise.

Figure 4:
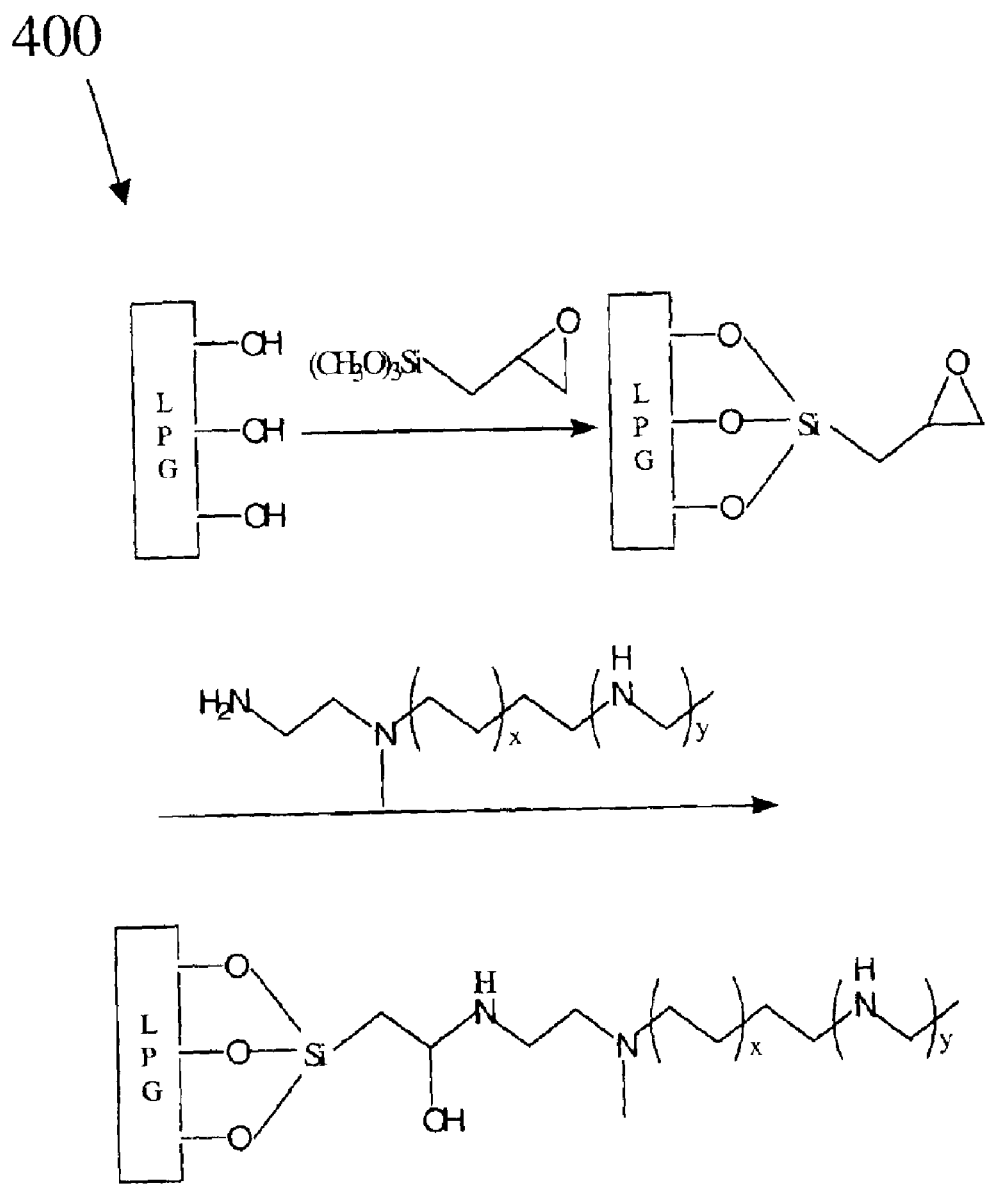
FIG. 4 is a schematic presentation of a chemical modification of an exemplary optical fiber surface of the present invention.

FIG. 4 is a schematic presentation 400 of a chemical modification of an exemplary optical fiber surface of the present invention. The chemical modification was performed on an outer surface of a cladding of an optical fiber imprinted with LPG to form a moisture sensor.

In preparing the sensor, the outer surface of an uncoated portion of an LPG imprinted fiber was cleaned with 20% NaOH/ethanol (v/v=1:1) for 2 hours and washed with de-ionized water. The LPG portion was treated with 2 M HCl for 4 hours to introduce OH groups on the surface, washed with de-ionized water and ethanol, successively, and dried. The LPG portion was immersed in 10% 3-glycidoxypropyl trimethoxysilane (available from Aldrich of Milwaukee, Wis.) ethanol solution in a nitrogen environment for 6 hours, and washed with ethanol. Prior to use, the silanized LPG portion was reacted with 2% polyethylenimine (PEI) (having a molecular weight of 7500, and available from Aldrich of Milwaukee, Wis.) for 18 hours and washed with de-ionized water. A higher molecular weight PEI (Mw=750,000) was also used to construct LPG moisture sensors.

The PEI layer on an LPG sensor can react with the environmental moisture through hydrogen bonding. As a result, the polymer layer can swell resulting in a change of the polymer layer thickness and density, and therefore the refractive index of the polymer coating, as demonstrated from the spectrum output of the sensor. The device used for calibrating this moisture sensor was constructed in our laboratory with a commercial hygrometer (available from Fisher Scientific of Pittsburgh, Pa.) to calibrate relative humidity in the chamber.

Figure 5:
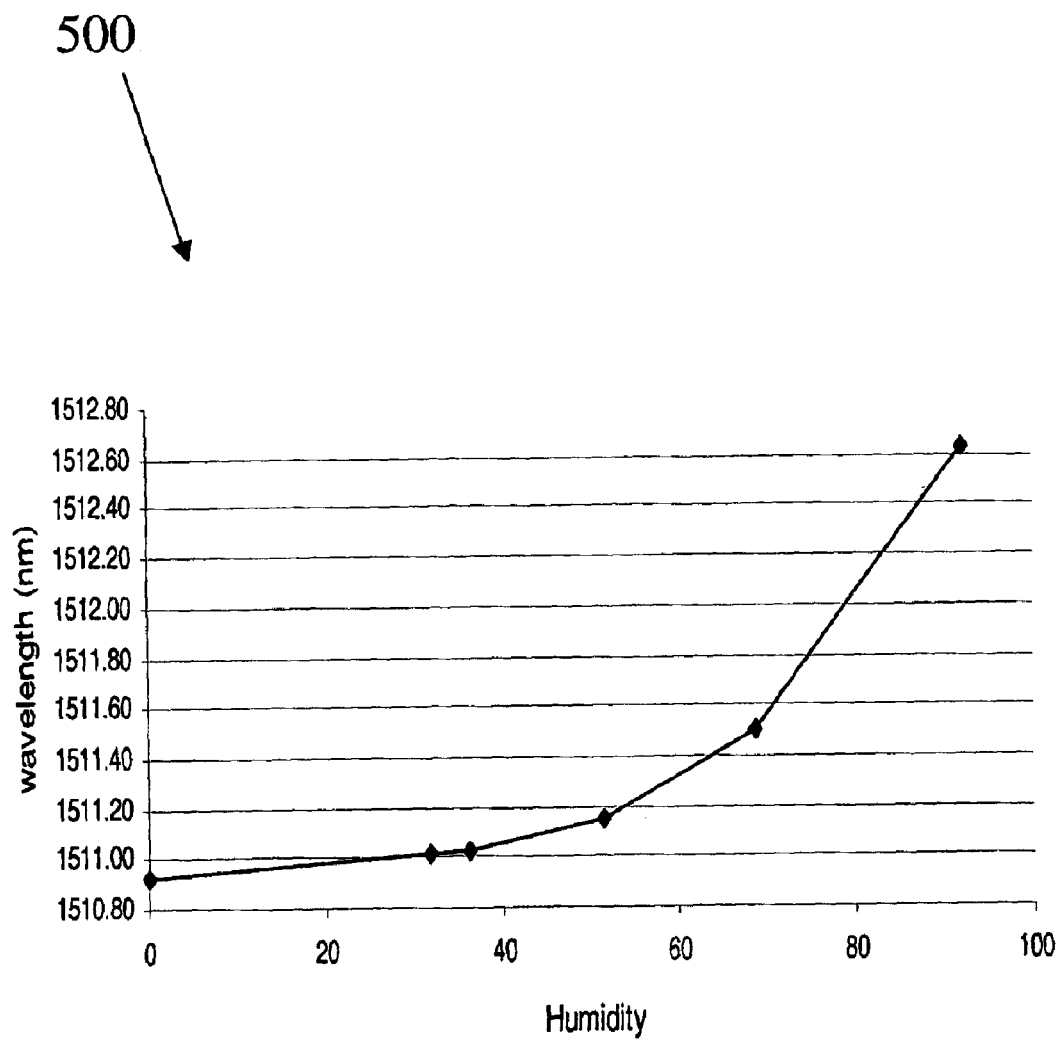
FIG. 5 is a calibration curve for an exemplary moisture sensor of the present invention.

FIG. 5 is a calibration curve 500 for an exemplary moisture sensor of the present invention. FIG. 5 shows wavelength shift versus humidity level. As shown, this sensor (with PEI molecular of 7500) is more sensitive towards higher humidity levels than lower humidity levels.

Figure 6:
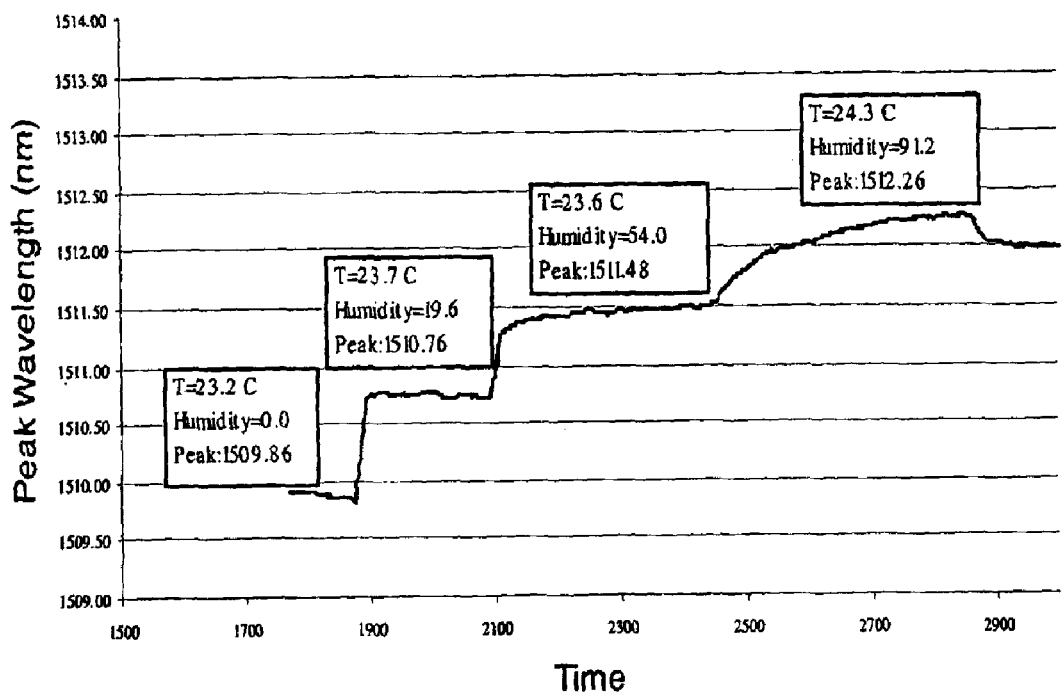
FIG. 6 is a data log showing the response of an exemplary moisture sensor of the present invention to various levels of moisture.

FIG. 6 is a data log showing the response of an exemplary moisture sensor of the present invention to various levels of moisture. FIG. 6 was copied from a computer screen and shows the response of the sensor to relative humidity varying from 0.0% to 91.2%.

Figure 7:
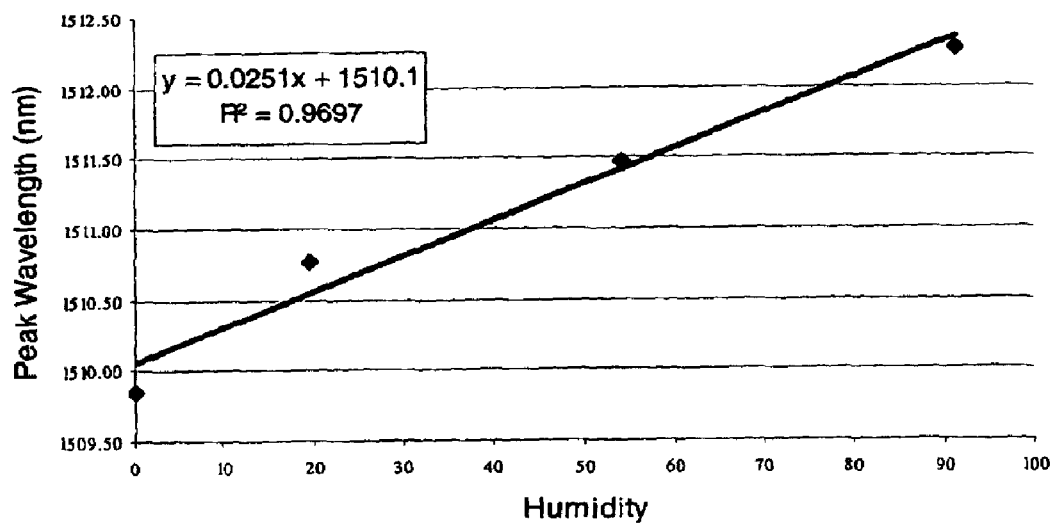
FIG. 7 is a response curve for an exemplary moisture sensor of the present invention.

FIG. 7 is a response curve for an exemplary moisture sensor of the present invention. The response was linear from 0.0% to 91.2% of the humidity level with $R^2$ equals 0.9697. It is observed that the calibration curves for the two sensors having PEI of different molecular weights are different. The curve for the sensor with molecular weight of 7500 is not linear while the one with molecular weight of 750,000 is linear over the whole moisture range. The sensitivity of the sensor can be fine-tuned towards different ranges of humidity by using PEI with different molecular weights. The reliability of the sensor was tested by repeatedly changing the moisture content in the chamber from 0% to 90% while keeping the chamber temperature as constant as possible.

Figure 8:
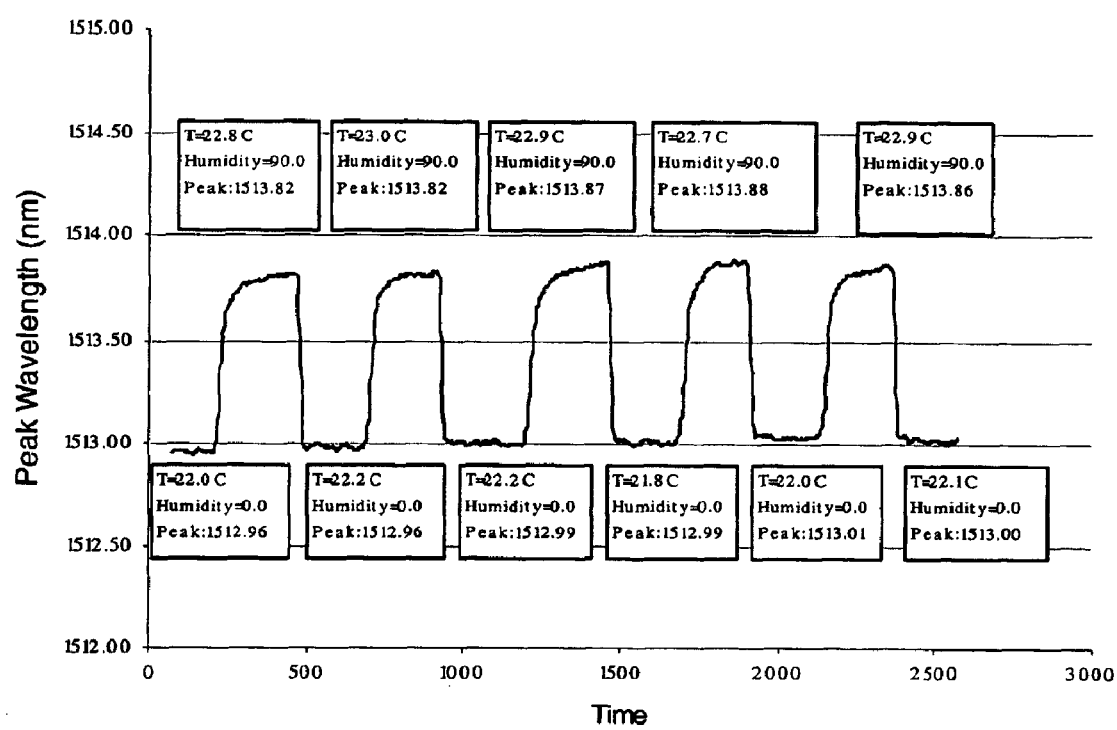
FIG. 8 is a graph for an exemplary moisture sensor of the present invention wherein humidity oscillates between two levels.

FIG. 8 is a graph for an exemplary moisture sensor of the present invention wherein humidity oscillates between two levels. As shown in FIG. 8, humidity varies between 0.0 and 90.0%. The relative standard deviations were 2.8% for a 0.0% humidity level and 1.9% for a 90.0% humidity level, respectively.

Figure 9:
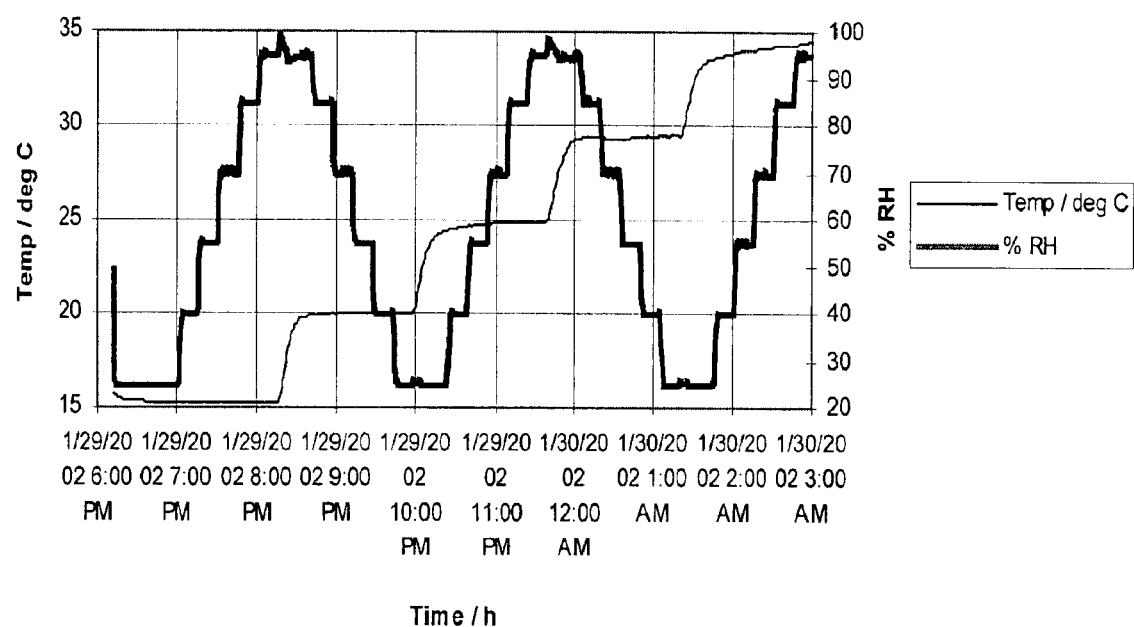
FIG. 9 is a data log for temperature and relative humidity versus time for an exemplary moisture sensor of the present invention.

FIG. 9 is a data log for temperature and relative humidity versus time for an exemplary moisture sensor of the present invention. FIG. 9 further reflects the method by which the Thunder Scientific Humidity Generator was programmed for operation. The temperature was ramped up in 5-degree steps from 15° C. to 35° C. while humidity levels were increased or decreased stepwise at each temperature setting.

Figure 10:
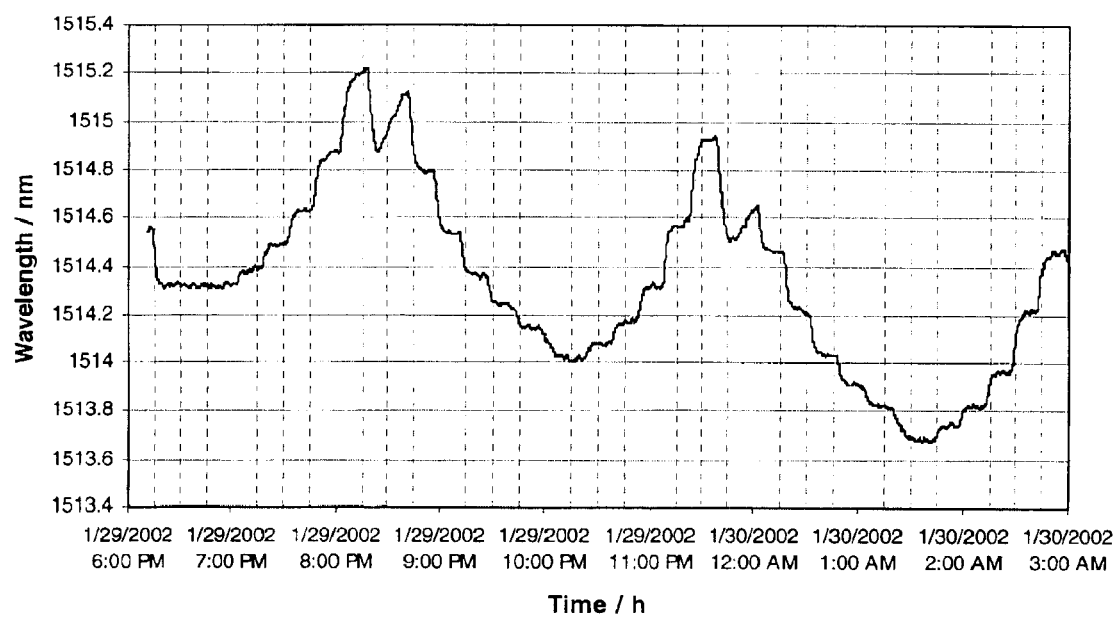
FIG. 10 is a chart reflecting a steady-state response of an exemplary chamber.

FIG. 10 is a chart reflecting a steady-state response of an exemplary moisture sensor of the present invention to conditions within an environmental chamber. The conditions within the environment chamber were described above, and the steady-state response values of the chart of FIG. 10 are listed in Table 1, below.

After stabilization of temperature, the humidity within the chamber was increased step-wise from 25%, through 40%, 55%, 70%, 85%, and up to 95%. Following a 15-minute stabilization period, an increase in temperature was initiated while maintaining constant RH. When the temperature stabilized at the new value, humidity was decreased. This sequence was repeated until the highest programmed temperature was reached. Simultaneously, continuous measurements (in 10-second intervals) as shown in the sensogram (FIG. 10) were performed with the PEI-coated humidity sensor.

TABLE 1

Response (at steady state) from a polyethyleneimine coated LPG humidity sensor.

| time (hrs) | RH (%) | Temp. (deg C.) | Wavelength (nm) |
| --- | --- | --- | --- |
| 0.833389 | 25.44 | 15.25 | 1514.33 |
| 1.067222 | 39.99 | 15.25 | 1514.40 |
| 1.334722 | 55.16 | 15.24 | 1514.51 |
| 1.584722 | 69.99 | 15.24 | 1514.64 |
| 1.835000 | 84.96 | 15.24 | 1514.90 |
| 2.085556 | 94.95 | 15.24 | 1515.21 |
| 2.517222 | 94.02 | 19.84 | 1515.11 |
| 2.750556 | 84.93 | 19.94 | 1514.79 |
| 3.017500 | 69.97 | 19.97 | 1514.52 |
| 3.268055 | 54.98 | 19.99 | 1514.38 |
| 3.518333 | 39.98 | 19.99 | 1514.24 |
| 3.835556 | 25.29 | 20.60 | 1514.15 |
| 4.202778 | 25.02 | 24.40 | 1514.02 |
| 4.450555 | 39.97 | 24.66 | 1514.10 |
| 4.701111 | 54.97 | 24.78 | 1514.19 |
| 4.951389 | 69.98 | 24.85 | 1514.33 |
| 5.201944 | 85.05 | 24.88 | 1514.59 |
| 5.450278 | 95.00 | 24.92 | 1514.92 |
| 5.883611 | 94.84 | 29.29 | 1514.64 |
| 6.133611 | 84.98 | 29.35 | 1514.45 |
| 6.383889 | 69.98 | 29.27 | 1514.19 |
| 6.634444 | 54.89 | 29.41 | 1514.02 |
| 6.901945 | 39.82 | 29.46 | 1513.89 |
| 7.185278 | 25.52 | 29.53 | 1513.80 |
| 7.583611 | 25.24 | 33.56 | 1513.70 |
| 7.834167 | 40.18 | 33.84 | 1513.76 |
| 8.084167 | 55.01 | 34.00 | 1513.83 |
| 8.234444 | 69.97 | 34.20 | 1513.96 |
| 8.585000 | 85.07 | 34.25 | 1514.26 |
| 8.835278 | 94.96 | 34.48 | 1514.45 |

Figure 11:
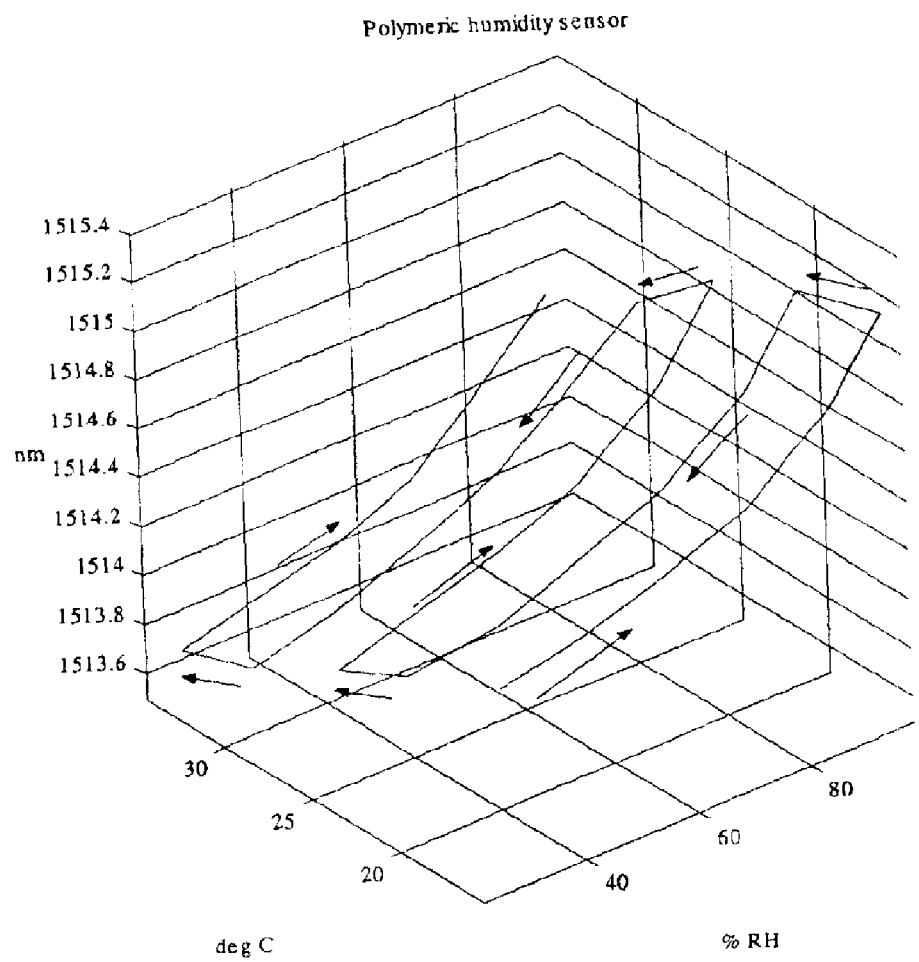
FIG. 11 is a record for an exemplary moisture sensor of the present invention reacting to conditions within an environment chamber.

FIG. 11 is a record for an exemplary moisture sensor of the present invention reacting to conditions within an environment chamber. FIG. 11 provides a graph showing a three-dimensional plot of the steady state values of the LPG wavelength as a function of relative humidity and temperature, as listed in Table 1.

Figure 12:
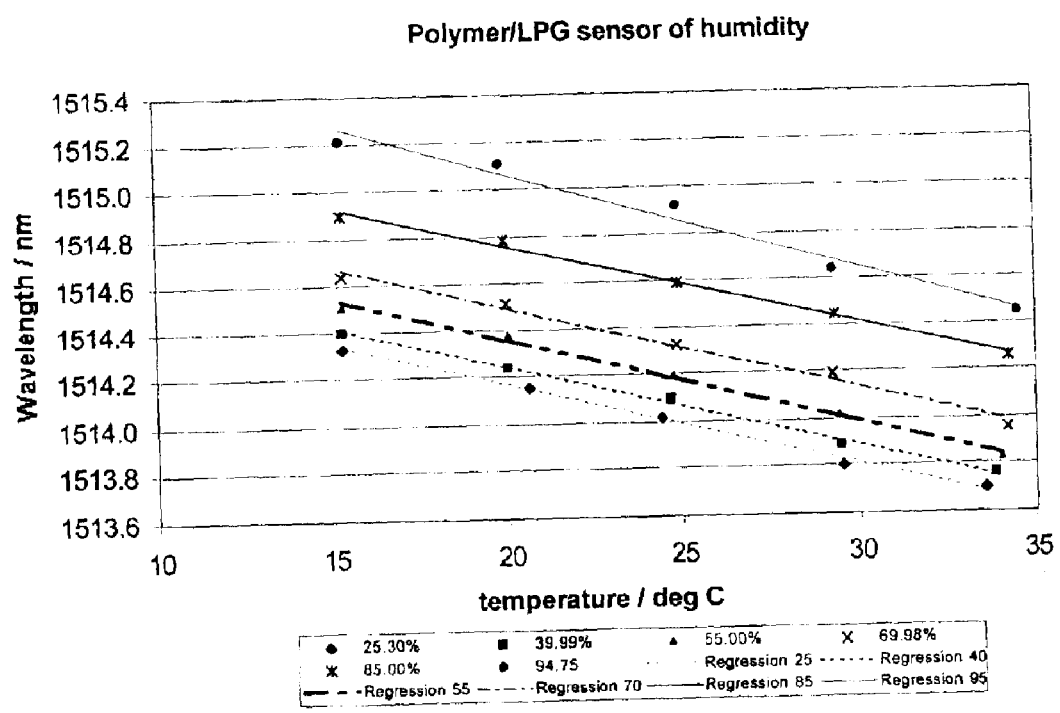
FIG. 12 is a graph of steady-state values of LPG wavelength as a function of relative humidity and temperature for an exemplary moisture sensor of the present invention.

FIG. 12 is a graph of steady-state values of LPG wavelength as a function of relative humidity and temperature for an exemplary moisture sensor of the present invention. As can be inferred from inspection of FIG. 12, the temperature effect on the indicated wavelength is nearly linear and can be easily corrected for with collocated measurement of temperature. FIG. 12 also contains linear regression results for each RH level. These results further support the assertion that temperature variation of the wavelength indicated by the LPG moisture sensor is linear and virtually invariant with humidity.

Figure 13:
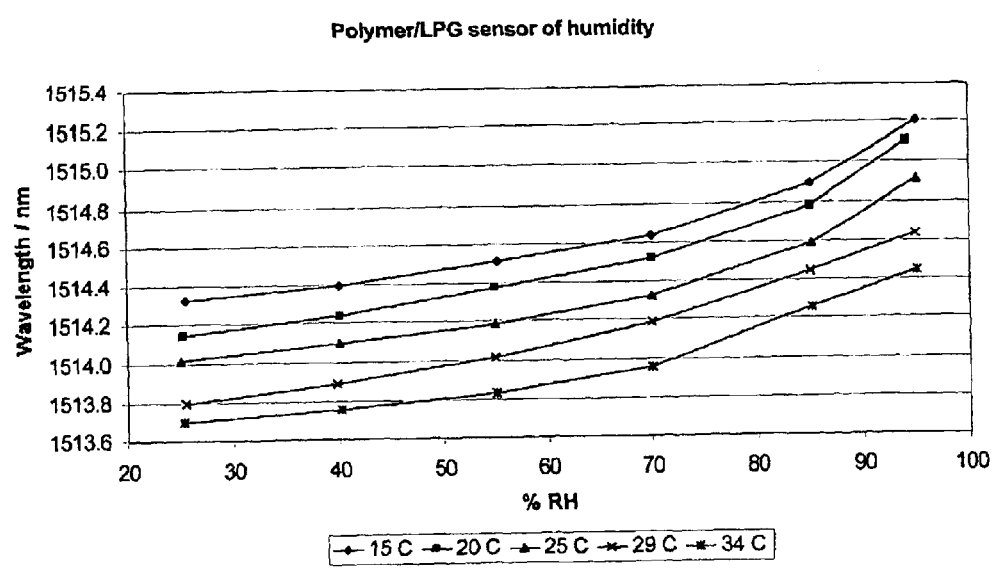
FIG. 13 is a graph of temperature dependence of wavelength output by an exemplary moisture sensor of the present invention.

FIG. 13 is a graph of temperature dependence of wavelength output by an exemplary moisture sensor of the present invention. FIG. 13 includes a family of curves showing a shift of the wavelength indicated by the sensor as a function of Relative Humidity at different temperatures. The characteristic response of this type of sensor to % RH is nearly parabolic. This nonlinear response does not present a significant computational obstacle, since the possibility of a quadratic response was anticipated and a second-order polynomial fit can be provided by the control software. That control software can specifically address the collocated to measurements of temperature and other parameters, such as relative humidity. By implementing this solution, sensors can be offered for embedded collocated measurements of physical parameters.

Method 14000

Figure 14:
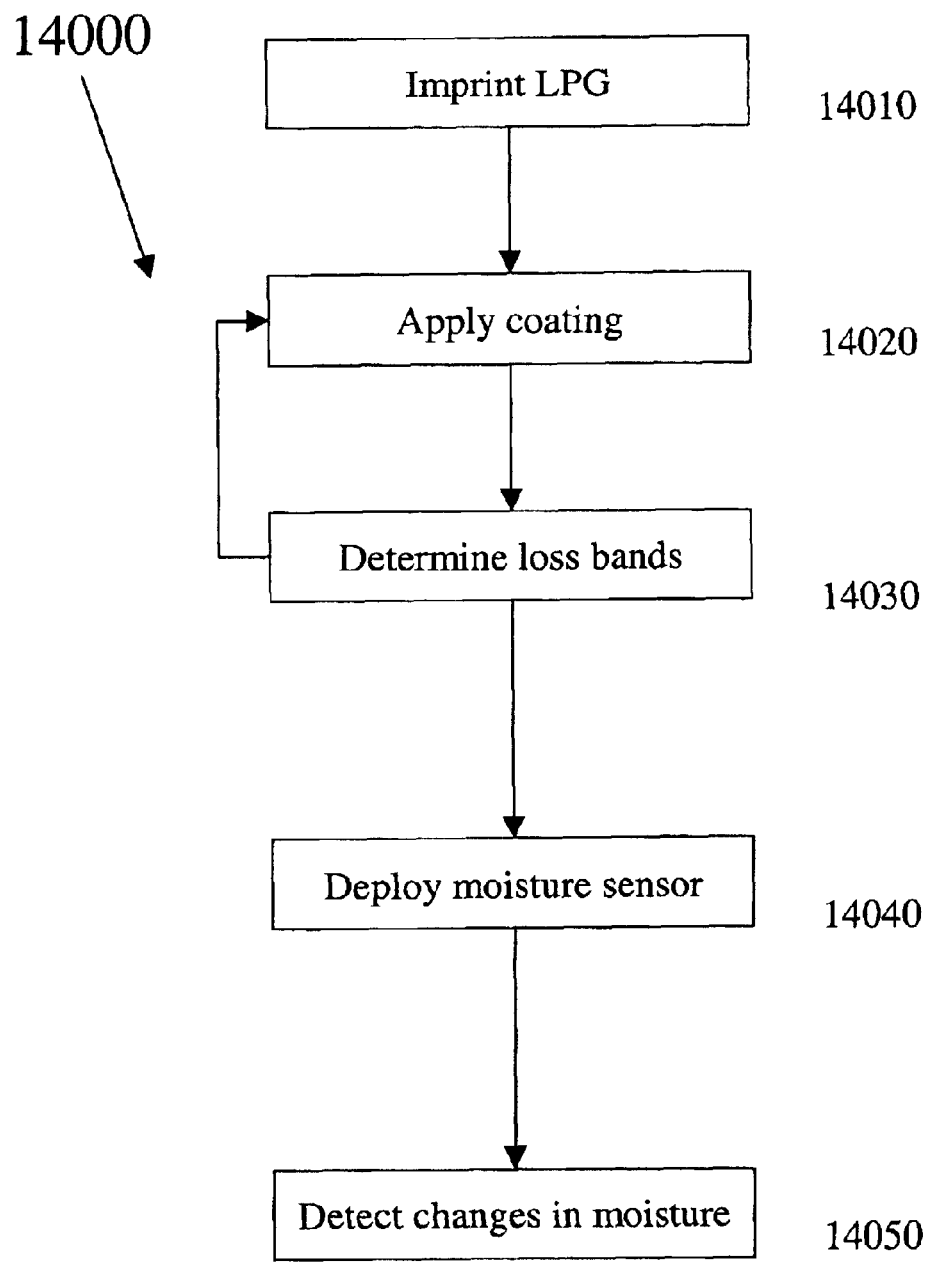
FIG. 14 is a flowchart of an exemplary method 14000 of the present invention.

FIG. 14 is a flowchart of an exemplary embodiment of a method 14000 of the present invention. Method 14000 can begin at activity 14010 by imprinting an LPG on the core of an optical fiber. At activity 14020, a PEI coating can be applied to the LPG fiber. At activity 14030, loss bands for the coated LPG fiber can be determined at a reference humidity level. At this point, the coated LPG fiber can be calibrated if desired. At activity 14040, the coated LPG fiber can be deployed as a moisture sensor. At activity 14050, changes in moisture level can be sensed using the coated LPG fiber.

There can be a number of applications of such an LPG moisture sensor. For example, an LPG moisture sensor can be associated with any of a number of structures, such as a building, a machine, a piece of equipment, an aircraft, a ship, a vehicle, a military equipment, a storage vessel, a pipeline, a bridge, and/or an electrical conduit. In the case of a building such as a home, numerous LPG moisture sensors can be installed in exterior walls, interior walls, ceilings, and/or floors, to sense otherwise hidden moisture. In the case of exterior dwelling walls, such LPG moisture sensors can sense water that has penetrated the exterior wall due to, for example, a failed caulking joint, faulty flashing, and/or improperly installed and/or maintained roofing system, etc. In the case of interior dwelling walls and/or ceilings, such LPG moisture sensors can sense water that is due to, for example, a faulty and/or failed plumbing conduit (e.g., pipe, tube, fitting, etc.) and/or fixture, poorly insulated air conditioning tubing, and/or upper floor spill, leaky roof, etc. In the case of dwelling floors, such LPG moisture sensors can sense water that is due to, for example, sewer failure, flooding, and/or clogging of exterior drainage systems, etc.

In the case of a pipeline, storage tank, and/or equipment, such LPG moisture sensors can sense water that is due to, for example, a failed thermal insulation jacketing system, inadequate insulation that leads to condensation, and/or leaks in a fluid conveyance system component (pipeline, fitting, valve, vessel, pump, and/or equipment, etc.).

In the case of an aircraft, such LPG moisture sensors can sense water that is due to, for example, condensation, the leaking of water into the aircraft, and/or the leaking of water out of the aircraft and/or a fluid conveyance system component of the aircraft.

System 15000

Figure 15:
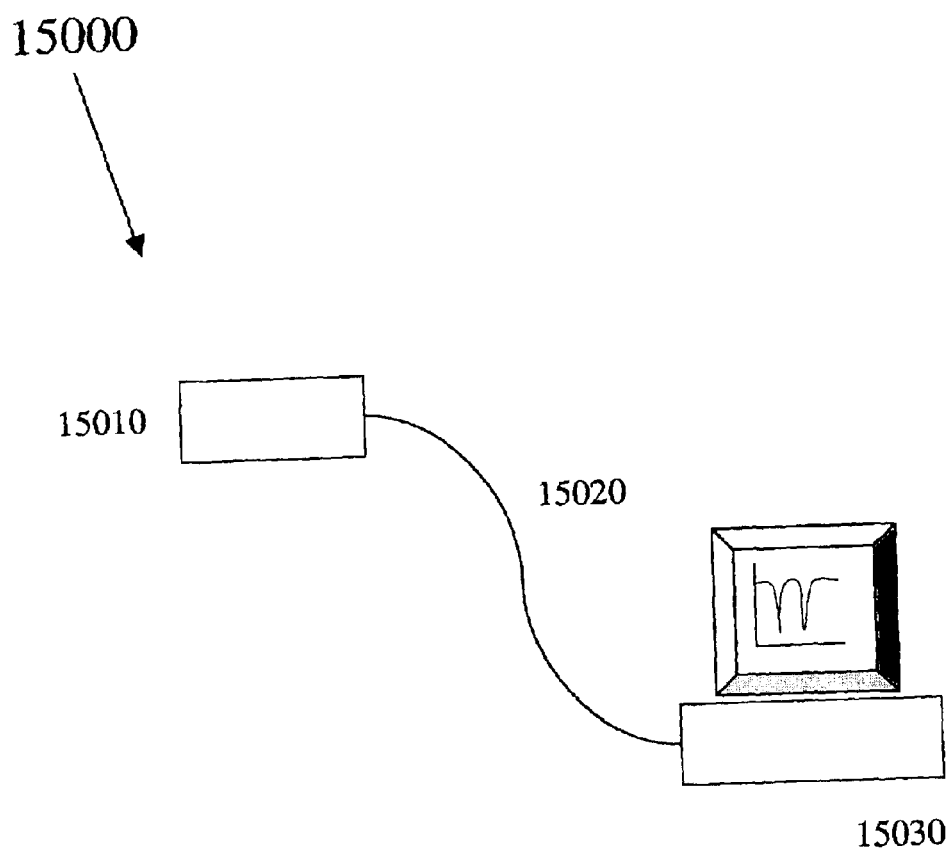
FIG. 15 is a diagram of an exemplary system 15000 of the present invention.

FIG. 15 is a diagram of an exemplary embodiment of a system 15000 of the present invention that can be useful for sensing changes in moisture. A light source 15010 can be optically coupled to a PEI-coated LPG optical fiber 15020, which can be optically coupled to an optical spectrum analyzer 15030.

It should be understood that the preceding is merely a detailed description of one or more exemplary embodiments of this invention and that numerous changes to the disclosed embodiments can be made in accordance with the disclosure herein without departing from the spirit or scope of the invention. The preceding description, therefore, is not meant to limit the scope of the invention. Rather, the scope of the invention is to be determined only by the appended claims, every element of which can be replaced by any one of numerous equivalent alternatives without departing from the spirit or scope of the invention, only some of which equivalent alternatives are disclosed in the specification.

What is claimed is:

1. A moisture sensor comprising:
    an optical fiber;
    a long period grating formed in at least a portion of said optical fiber; and
    a layer of polyethylenimine (PEI) bonded to said long period grating.

2. A fiber optic moisture sensor having a covalently-bonded polyethylenimine (PEI) mono-layer.

3. An optical fiber moisture sensor having a mono-layer of polyethylenimine (PEI) covalently-bonded to an outer surface of said optical fiber.

4. A mono-layer of polyethylenimine (PEI) covalently-bonded to an outer surface of an optical fiber moisture sensor.

5. A moisture sensor comprising:
    an optical fiber; and
    a mono-layer of polyethylenimine (PEI) covalently-bonded to an outer surface of said optical fiber.

6. The moisture sensor of claim 5, wherein a molecular weight of said polyethylenimine (PEI) is within a range of approximately 7500 to approximately 1,000,000.

7. The moisture sensor of claim 5, wherein a molecular weight of said polyethylenimine (PEI) is above 7500.

8. The moisture sensor of claim 5, wherein a molecular weight of said polyethylenimine (PEI) is less than 1,000,000.

9. A moisture sensor embedded in a building material, said moisture sensor comprising an optical fiber having a mono-layer of polyethylenimine (PEI) covalently-bonded to an outer surface of said optical fiber.

10. A moisture sensor attached to a building material, said moisture sensor comprising an optical fiber having a mono-layer of polyethylenimine (PEI) covalently-bonded to an outer surface of said optical fiber.

11. A moisture sensor associated with a structure, said moisture sensor comprising an optical fiber having a mono-layer of polyethylenimine (PEI) covalently-bonded to an outer surface of said optical fiber.

12. The moisture sensor of claim 11, wherein said structure is a building.

13. The moisture sensor of claim 11, wherein said structure is a machine.

14. The moisture sensor of claim 11, wherein said structure is an equipment.

15. The moisture sensor of claim 11, wherein said structure is an aircraft.

16. The moisture sensor of claim 11, wherein said structure is a ship.

17. The moisture sensor of claim 11, wherein said structure is a vehicle.

18. The moisture sensor of claim 11, wherein said structure is a military equipment.

19. The moisture sensor of claim 11, wherein said structure is a storage vessel.

20. The moisture sensor of claim 11, wherein said structure is a pipeline.

21. The moisture sensor of claim 11, wherein said structure is a bridge.

22. The moisture sensor of claim 11, wherein said structure is an electrical conduit.

23. A system for measuring humidity, comprising:
    optical fiber moisture sensor having a mono-layer of polyethylenimine (PEI) covalently-bonded to an outer surface of said optical fiber;
    a processor coupled to said optical fiber moisture sensor; and
    a moisture indicator coupled to said processor.

24. A system for predicting mold growth, comprising:
    optical fiber moisture sensor having a mono-layer of polyethylenimine (PEI) covalently-bonded to an outer surface of said optical fiber;

a processor coupled to said optical fiber moisture sensor; and a mold growth indicator coupled to said processor.

25. A system for predicting corrosion, comprising:

optical fiber moisture sensor having a mono-layer of polyethylenimine (PEI) covalently-bonded to an outer surface of said optical fiber;

a processor coupled to said optical fiber moisture sensor; and a corrosion indicator coupled to said processor.

26. A method for fabricating a moisture sensor, comprising:

forming a long period grating in a core of an optical fiber; and covalently-bonding a mono-layer of polyethylenimine (PEI) to an outer surface of a cladding of the optical fiber.

27. The method of claim 26, further comprising:

stripping a covering from the cladding in the vicinity of the long period grating.

28. The method of claim 26, further comprising:

saturating the core with hydrogen.

29. The method of claim 26, further comprising:

applying a mask to a portion of the core.

30. The method of claim 26, further comprising:

exposing an unmasked portion of the core to a refraction index-changing source of light.

31. The method of claim 26, further comprising:

exposing an unmasked portion the core to a source of ultraviolet light.

32. The method of claim 26, further comprising:

imprinting the long period grating onto the core.

33. The method of claim 26, further comprising:

forming the mono-layer of polyethylenimine (PEI).

34. The method of claim 26, further comprising:

annealing the core to remove excess hydrogen.

35. The method of claim 26, further comprising:

identifying a loss band of light transmitted past the long period grating.

36. The method of claim 26, further comprising:

exposing the moisture sensor to a variation in ambient humidity.

37. The method of claim 26, further comprising:

monitoring a loss band of light transmitted past the long period grating.

38. The method of claim 26, further comprising:

quantifying a change in a loss band of light transmitted past the long period grating.

39. The method of claim 26, further comprising:

correlating a change in a loss band of light transmitted past the long period grating with a moisture level.

40. The method of claim 26, further comprising:

indicating a moisture level.

* * * * *